United States Patent
Zhang et al.

(10) Patent No.: US 11,260,163 B2
(45) Date of Patent: Mar. 1, 2022

(54) ANTI-REFLUX NASAL ASPIRATOR

(71) Applicant: Ningbo Albert Novosino Co., Ltd, Ningbo (CN)

(72) Inventors: Yonggui Zhang, Ningbo (CN); Haibo Hu, Ningbo (CN)

(73) Assignee: NINGBO ALBERT NOVOSINO CO., LTD., Ningbo (CN)

( * ) Notice: Subject to any disclaimer, the term of this patent is extended or adjusted under 35 U.S.C. 154(b) by 170 days.

(21) Appl. No.: 16/600,964

(22) Filed: Oct. 14, 2019

(65) Prior Publication Data

US 2020/0306425 A1 Oct. 1, 2020

(30) Foreign Application Priority Data

Mar. 31, 2019 (CN) .......................... 201920422478.1
Jun. 19, 2019 (CN) .......................... 201930319840.8

(51) Int. Cl.
*A61M 1/00* (2006.01)
*A61B 17/24* (2006.01)

(52) U.S. Cl.
CPC .............. *A61M 1/78* (2021.05); *A61B 17/24* (2013.01); *A61M 1/741* (2021.05); *A61M 1/86* (2021.05); *A61B 2017/246* (2013.01); *A61M 2205/075* (2013.01); *A61M 2210/0618* (2013.01)

(58) Field of Classification Search
CPC .................. A61M 1/0003; A61M 1/82; A61M 2205/075; A61M 2210/0618; A61M 3/0262
See application file for complete search history.

(56) References Cited

U.S. PATENT DOCUMENTS

| | | | | |
|---|---|---|---|---|
| 2,655,918 | A * | 10/1953 | Maldwyn | A61M 11/06 128/200.22 |
| 2,890,699 | A * | 6/1959 | Miller | A61M 1/0003 604/213 |
| 3,618,846 | A * | 11/1971 | Poli | B23K 1/018 228/52 |
| 3,892,226 | A * | 7/1975 | Rosen | A61M 3/0229 600/563 |
| 4,487,336 | A * | 12/1984 | Sneider | A61M 3/0262 222/107 |
| 4,801,292 | A * | 1/1989 | Watson | A61M 3/0229 604/36 |

(Continued)

OTHER PUBLICATIONS

Baby Nasal Aspirator, Amazon.com (last visited: Oct. 14, 2019).

(Continued)

*Primary Examiner* — Scott J Medway
(74) *Attorney, Agent, or Firm* — Thomas | Horstemeyer, LLP

(57) ABSTRACT

Disclosed are various embodiments for an anti-reflux nasal aspirator that includes a nozzle comprising a nozzle outlet, a bulb configured to provide suction at the nozzle outlet in response to a squeezing force applied to the bulb, an anti-reflux coupler positioned between the bulb and the nozzle through which air passes from the bulb to the nozzle, and a one-way air valve positioned in an aperture located at a base of the bulb. The anti-reflux coupler may include a check valve configured to prevent reflux of debris into the bulb. The check valve may include one of an umbrella valve; a duckbill valve; a slit-cutting valve; and a flapper valve.

20 Claims, 7 Drawing Sheets

(56) References Cited

U.S. PATENT DOCUMENTS

| | | | | |
|---|---|---|---|---|
| 5,062,835 A * | 11/1991 | Maitz | ............ | A61M 1/0023 604/153 |
| 5,318,548 A * | 6/1994 | Filshie | ............ | A61M 1/0003 604/319 |
| 6,491,940 B1 * | 12/2002 | Levin | ............ | A61K 31/445 424/434 |
| 7,300,424 B1 * | 11/2007 | Mulford | ............ | A61M 1/82 604/319 |
| 7,435,252 B2 * | 10/2008 | Krespi | ............ | A61B 18/18 128/898 |
| 8,181,651 B2 * | 5/2012 | Pinel | ............ | A61M 16/047 128/205.19 |
| 8,696,648 B2 * | 4/2014 | Laerdal | ............ | A61M 1/0003 604/540 |
| 8,827,945 B2 * | 9/2014 | Baker | ............ | A61M 1/0062 604/35 |
| 9,433,724 B2 * | 9/2016 | Rubin | ............ | A61M 3/0283 |
| 9,656,005 B2 * | 5/2017 | Varney | ............ | A61M 1/0003 |
| 10,265,462 B2 * | 4/2019 | Layer | ............ | A61M 3/0283 |
| D897,525 S * | 9/2020 | Zhang | ............ | A61M 1/741 D24/115 |
| 10,888,673 B2 * | 1/2021 | Trevino | ............ | A61M 11/008 |
| 2007/0027433 A1 * | 2/2007 | Garcia | ............ | A61M 1/63 604/319 |
| 2008/0154183 A1 * | 6/2008 | Baker | ............ | A61M 3/0216 604/28 |
| 2011/0319840 A1 * | 12/2011 | Hair | ............ | A61M 3/0262 604/275 |
| 2018/0228963 A1 * | 8/2018 | Mitchell | ............ | B65D 25/48 |

OTHER PUBLICATIONS

NoseFrida by Frida Baby, Baby Nasal Aspirator, Amazon.com (last visited: Oct. 14, 2019).

BoogieBulb Baby Nasal Aspirator for Newborns Toddlers & Adult, Amazon.com (last visited: Oct. 14, 2019).

* cited by examiner

ANTI-REFLUX NASAL ASPIRATOR

CROSS-REFERENCE TO RELATED APPLICATIONS

This application claims the benefit of and priority to Chinese Patent Application No. 201930319840.8 filed Jun. 19, 2019 and Chinese Patent Application No. 201920422478.1 filed Mar. 31, 2019, the contents of which being incorporated by reference in their entireties herein.

TECHNICAL FIELD

This invention belongs to the technical field of nasal aspirators and, more specifically, describes an anti-reflux, leakproof, easy-to-discharge, and easy-to-clean nasal aspirator.

BACKGROUND

Nasal aspirators include devices that can be utilized by patients and medical practitioners for sucking debris from the nasal cavity and potentially other bodily cavities, such as the ear canal. Generally, nasal aspirators provide suction to remove debris from the nasal cavity of a person by hand squeezing a bulb or similar apparatus. During this process, the debris "refluxes," or moves into an interior of the bulb, which contaminates the bulb. The bulb is often difficult or impossible to clean as a nozzle of the nasal aspirator is integral with the bulb.

BRIEF SUMMARY OF INVENTION

Disclosed are various embodiments for an anti-reflux nasal aspirator that includes a nozzle comprising a nozzle outlet, a bulb configured to provide suction at the nozzle outlet in response to a squeezing force applied to the bulb, an anti-reflux coupler positioned between the bulb and the nozzle through which air passes from the bulb to the nozzle, and a one-way air valve positioned in an aperture located at a base of the bulb. The anti-reflux coupler may include a check valve configured to prevent reflux of debris into the bulb. The check valve may include one of an umbrella valve; a duckbill valve; a slit-cutting valve; and a flapper valve.

The anti-reflux nasal aspirator may further include a first connection for detachably attaching the anti-reflux coupler to the bulb and a second connection for detachably attaching the nozzle to the anti-reflux coupler. The first connection or the second connection can include one of a threaded connection and an interference fit connection. A first sealing ring may be provided that is configured to prevent leakage occurring at the first connection, and a second sealing ring may be provided that is configured to prevent leakage occurring at the second connection.

In some embodiments, the anti-reflux nasal aspirator includes a neck positioned between the nozzle and the bulb. The neck may include a reservoir positioned therein for storing debris pulled from the nozzle outlet. The reservoir may be at least partially nested in a top recess of the anti-reflux coupler. A reservoir lid may be positioned on a top portion of the reservoir, where the reservoir lid includes a projecting aperture for receiving debris.

The top recess of the anti-reflux coupler may include an air outlet and air channels notched in a perimeter of the top recess, where the air channels direct air around a side of the reservoir. In various embodiments, the neck includes a semi-circular base portion having a width substantially similar to a top neck of the bulb and a protruding portion having a width less than the width of the semi-circular base portion. The protruding portion can position the nozzle at a predetermined angle such as an angle equal to or less than 90 degrees.

The nozzle may be a first nozzle having a first predetermined size and shape. The nasal aspirator may further include a second nozzle having a second predetermined size and shape different from the first predetermined size and shape, the second nozzle being configured to replace the first nozzle via the second connection.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

DETAILED DESCRIPTION

Figure 1:
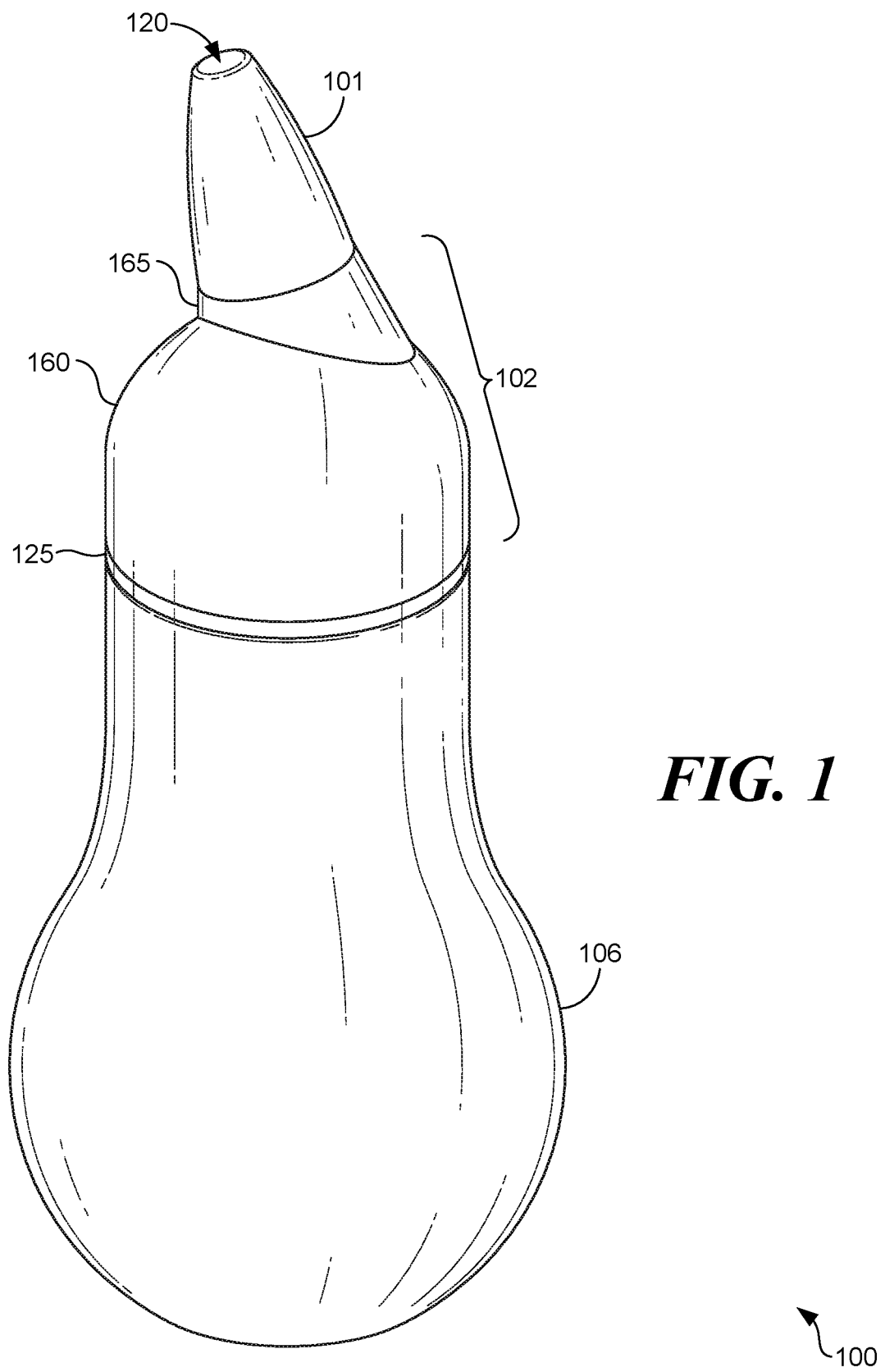
FIG. 1 is a perspective view of an anti-reflux nasal aspirator according to various embodiments of the present disclosure.

The present disclosure generally relates to an anti-reflux nasal aspirator that operates better than prior systems, and is easy to assemble and clean. Generally, nasal aspirators provide suction to remove debris from the nasal cavity of a person by hand squeezing a bulb or similar apparatus. During this process, the debris "refluxes," or moves into an interior of the bulb, which contaminates the bulb. The bulb is often difficult or impossible to clean as a nozzle of the nasal aspirator is integral with the bulb.

Accordingly, various embodiments are disclosed for an anti-reflux nasal aspirator that includes a nozzle comprising a nozzle outlet, a bulb configured to provide suction at the nozzle outlet in response to a squeezing force applied to the bulb, an anti-reflux coupler positioned between the bulb and the nozzle through which air passes from the bulb to the nozzle, and a one-way air valve positioned in an aperture located at a base of the bulb. The anti-reflux coupler may include a check valve configured to prevent reflux of debris into the bulb. The check valve may include one of an umbrella valve; a duckbill valve; a slit-cutting valve; and a flapper valve.

The anti-reflux nasal aspirator may further include a first connection for detachably attaching the anti-reflux coupler to the bulb and a second connection for detachably attaching the nozzle to the anti-reflux coupler. The first connection or the second connection can include one of a threaded connection and an interference fit connection. A first sealing ring may be provided that is configured to prevent leakage occurring at the first connection, and a second sealing ring may be provided that is configured to prevent leakage occurring at the second connection.

In some embodiments, the anti-reflux nasal aspirator includes a neck positioned between the nozzle and the bulb. The neck may include a reservoir positioned therein for storing debris pulled from the nozzle outlet. The reservoir may be at least partially nested in a top recess of the anti-reflux coupler. A reservoir lid may be positioned on a top portion of the reservoir, where the reservoir lid includes a projecting aperture for receiving debris.

The top recess of the anti-reflux coupler may include an air outlet and air channels notched in a perimeter of the top recess, where the air channels direct air around a side of the reservoir. In various embodiments, the neck includes a semi-circular base portion having a width substantially similar to a top neck of the bulb and a protruding portion having a width less than the width of the semi-circular base portion. The protruding portion can position the nozzle at a predetermined angle such as an angle equal to or less than 90 degrees.

The nozzle may be a first nozzle having a first predetermined size and shape. The nasal aspirator may further include a second nozzle having a second predetermined size and shape different from the first predetermined size and shape, the second nozzle being configured to replace the first nozzle via the second connection.

Referring now to FIG. 1, a perspective view of an anti-reflux nasal aspirator 100 is shown in accordance with various embodiments. The anti-reflux nasal aspirator 100 can include a nozzle 101, a neck 102, and a bulb 106 that are removably connected to one another. For instance, the nozzle 101 can be removed from the neck 102, the neck 102 can be removed from the bulb 106, and so forth. As such, in some embodiments, the nozzle 101 can be swapped with others having varying sizes and/or shapes. By virtue of an air valve positioned in the bulb 106, which will be discussed, an operator of the anti-reflux nasal aspirator 100 can continuously press the bulb 106 to non-stop sniffle, suck, or otherwise provide suction that removes debris from a cavity (e.g., nasal debris from a nasal cavity). Prior systems include bulbs that inflate rather slowly, which impairs operation of the aspirator and it unfriendly for use by the operator.

Figure 2:
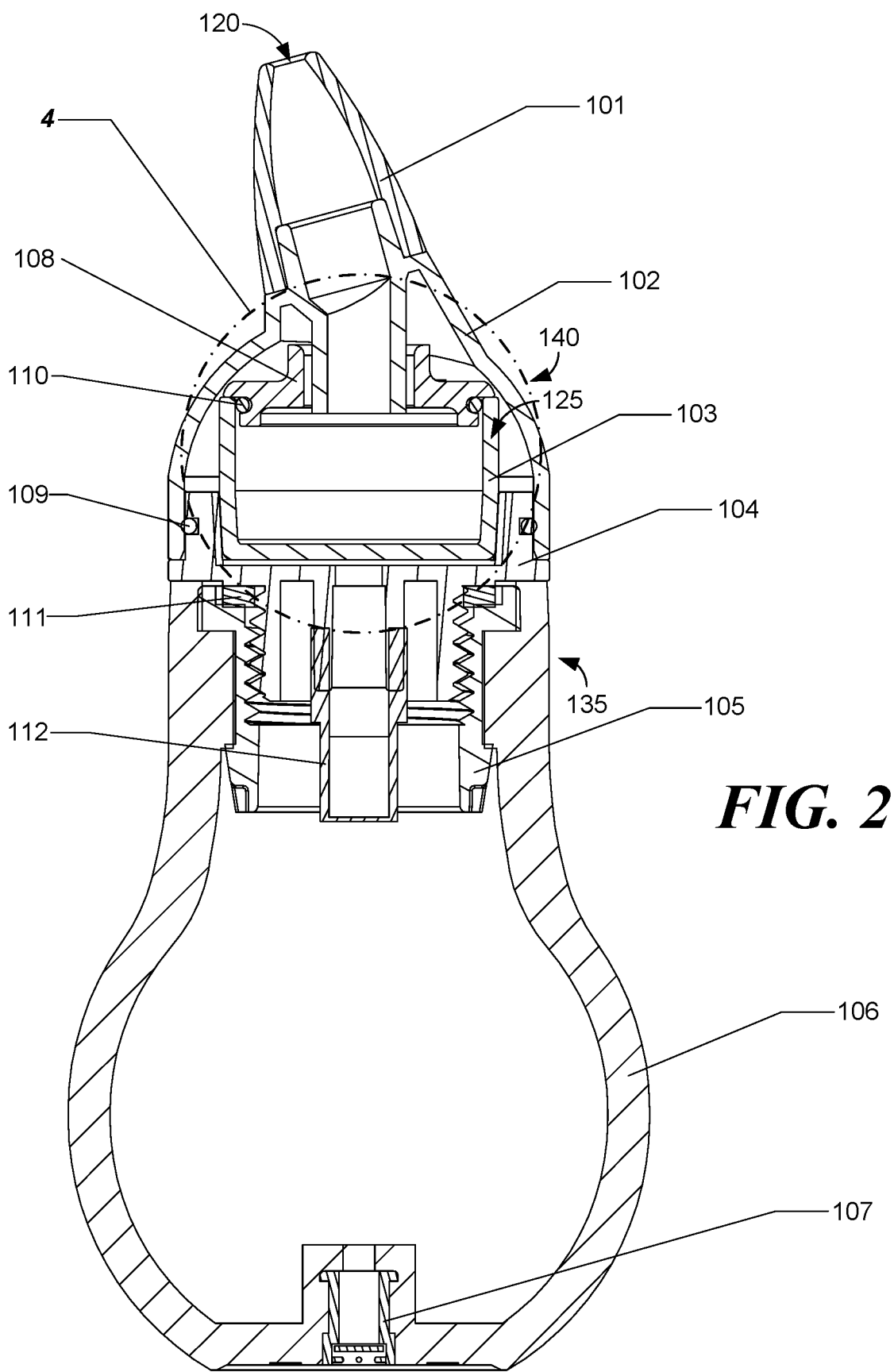
FIG. 2 is a cross-section view of the anti-reflux nasal aspirator according to various embodiments of the present disclosure.
Figure 3:
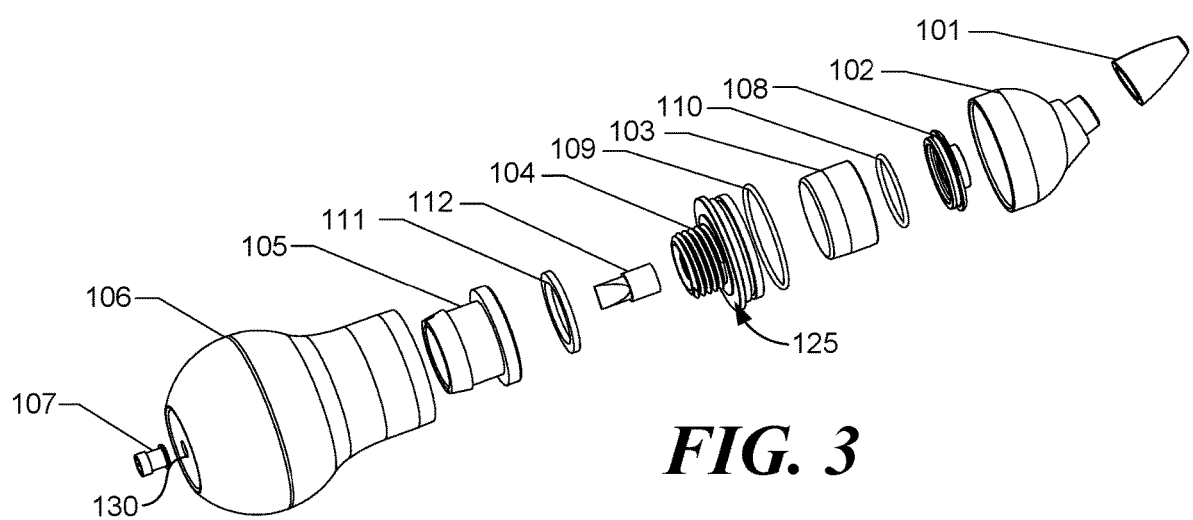
FIG. 3 is an exploded perspective view of the anti-reflux nasal aspirator according to various embodiments of the present disclosure.
Figure 4:
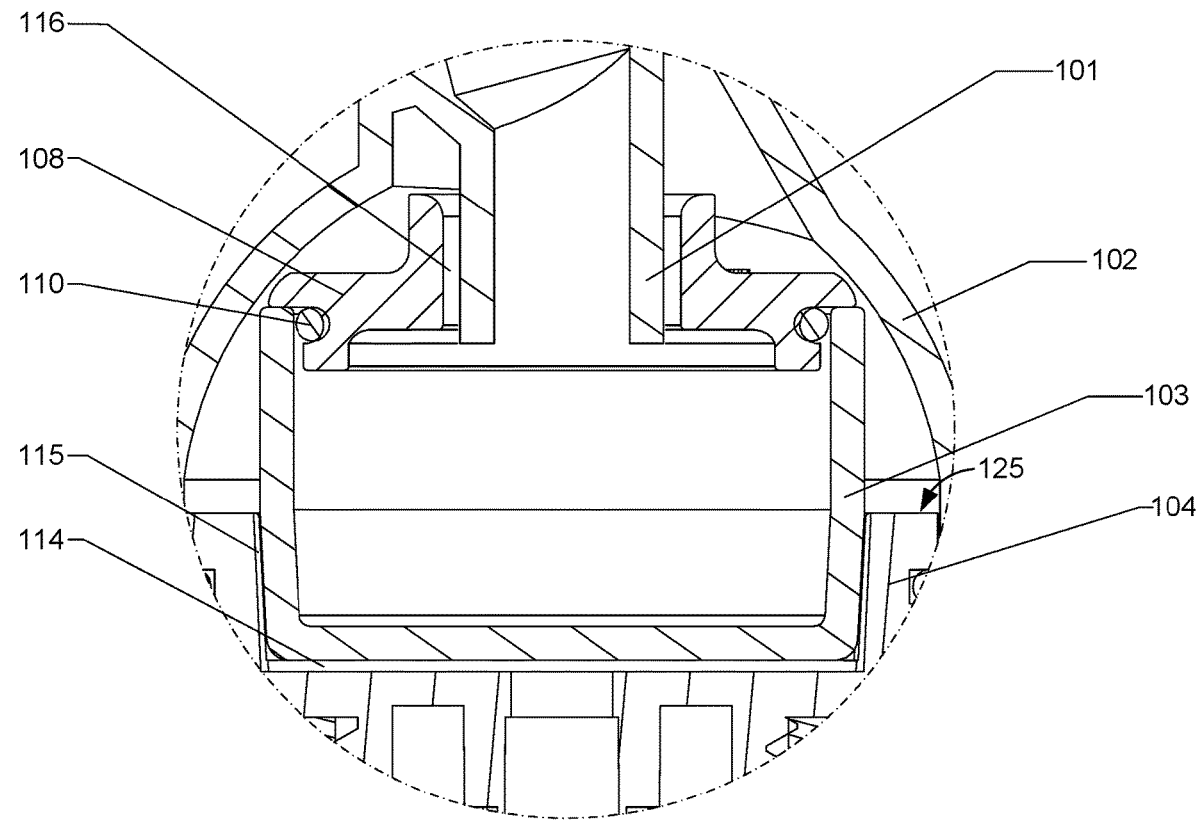
FIG. 4 is a partial enlarged view of callout region 4 of FIG. 1 according to various embodiments of the present disclosure.

Referring now to FIGS. 2 and 3, a cross-section view and an exploded view of the anti-reflux nasal aspirator 100 are shown, respectively. Referring to these figures collectively, the anti-reflux nasal aspirator 100 can include a nozzle 101, a neck 102, a reservoir 103 (e.g., a liquid storage cup), an external thread connector 104, an internal thread connector 105, a bulb 106, a one-way air valve 107, a reservoir lid 108, a first sealing ring 109, a second sealing ring 110, a washer 111, a check valve 112, a vent 113, a first vent groove 114, a second vent groove 115, a gap 116, a groove 117, and a nozzle outlet 120, as well as other components. FIG. 2 includes a cross-section view of the anti-reflux nasal aspirator 100. FIG. 1 includes callout region 4 of the cross-section view of FIG. 1 that is reproduced in an enlarged manner in FIG. 4.

Generally, the anti-reflux nasal aspirator 100 can include four principal components that are detachably attachable to one another, such as the nozzle 101, the neck 102, the bulb 106, and an anti-reflux coupler 125. As shown in the enlarged view of callout region 4 in FIG. 4, the anti-reflux coupler 125 includes the check valve 112, the first sealing ring 109, the external thread connector 104, which are shown relative to the nozzle 101, the neck 102, the reservoir 103, the reservoir lid 108, vent groove 114, vent groove 115, and gap 116.

Accordingly, the anti-reflux nasal aspirator 100 may include a nozzle 101 comprising a nozzle outlet 120, a bulb 106 configured to provide suction at the nozzle outlet 120, for instance, in response to a squeezing force applied to the bulb 106, and an anti-reflux coupler 125 positioned between the bulb 106 and the nozzle 101 through which air passes from the bulb 106 to the nozzle 101. Further, the anti-reflux nasal aspirator 100 may include a one-way air valve 107 positioned in an aperture 130 located at a base of the bulb 106.

The anti-reflux coupler 125 may include a check valve 112 configured to prevent reflux of debris into the bulb 106 or other upstream or downstream components. While in FIG. 3 the check valve 112 is illustrated as a duckbill valve, in various embodiments, the check valve 112 may include one of an umbrella valve, a duckbill valve, a slit-cutting valve, a flapper valve, or other suitable type of check valve 112.

The anti-reflux nasal aspirator 100 may further include a first connection 135 for detachably attaching the anti-reflux coupler 125 to the bulb 106 and a second connection 140 for detachably attaching the nozzle 101 to the anti-reflux coupler 125. The first connection 135 or the second connection 140 can include one of a threaded connection and an interference fit connection. For instance, in one embodiment, the first connection 135 can include a threaded connection and the second connection 140 can include an interference fit connection, or vice versa. As such, the first connection 135 can include the external thread connector 104 and the internal thread connector 105 in some embodiments.

A first sealing ring 109 may be provided that is configured to prevent leakage occurring at the first connection 135. Also, a second sealing ring 110 may be provided that is configured to prevent leakage occurring at the second connection 140. Other quantities of sealing rings 109, 110 may be provided based on a desired number of coupling and decoupling points.

In some embodiments, the anti-reflux nasal aspirator 100 includes a neck 102 positioned between the nozzle 101 and the bulb 106. The neck 102 may include a reservoir 103 positioned therein for storing snot, fluid, or other debris pulled from the nozzle outlet 120. The reservoir 103 may be at least partially nested in a top recess 160 of the anti-reflux coupler 125.

Figure 5:
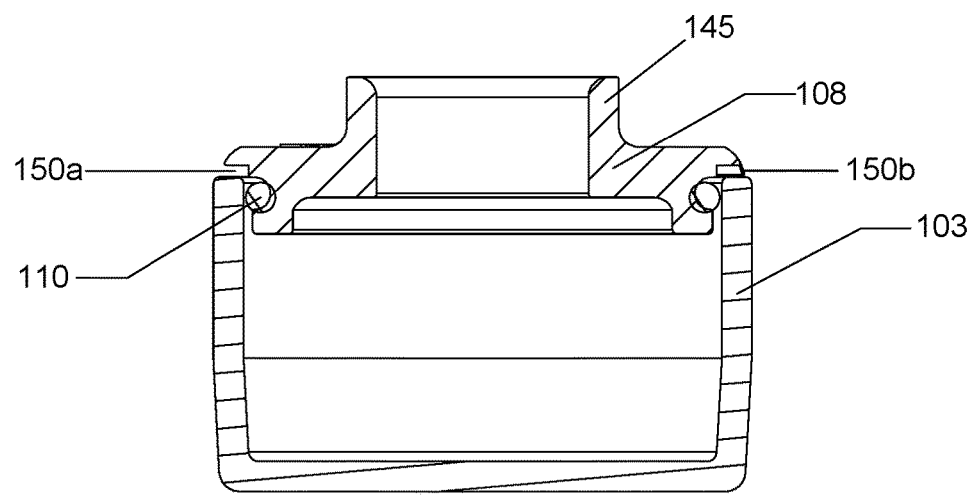
FIG. 5 is an enlarged cross-section view of a reservoir and a reservoir lid of the anti-reflux nasal aspirator according to various embodiments of the present disclosure.

A reservoir lid 108 (e.g., a liquid storage cup lid) may be positioned on a top portion of the reservoir 103, where the reservoir lid 108 includes an upwardly projecting aperture 145 for receiving debris. FIG. 5 is an enlarged cross-section view of a reservoir 103 and a reservoir lid 108 of the anti-reflux nasal aspirator 100 according to various embodiments of the present disclosure. As such, FIG. 5 shows a cross-section of the reservoir 103 relative to the reservoir lid 108, the second sealing ring 110, and the groove 117.

Figure 6:
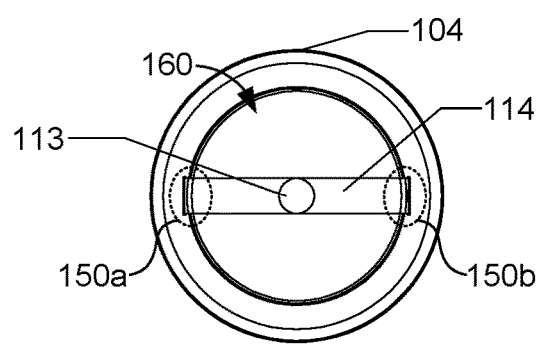
FIG. 6 is a plan view of an anti-reflux coupler according to various embodiments of the present disclosure.
Figure 7:
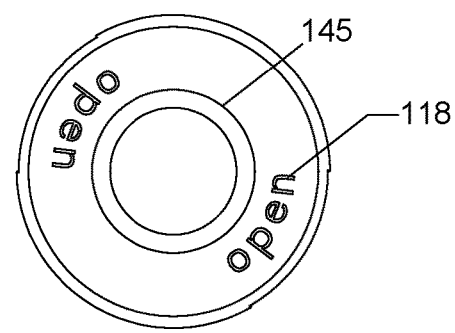
FIG. 7 is a plan view of the reservoir lid according to various embodiments of the present disclosure.

FIG. 6 illustrates a top plan view of an anti-reflux coupler 125 and FIG. 7 illustrates a top plan view of the reservoir lid 118 according to various embodiments of the present disclosure. Referring specifically to FIG. 5 and FIG. 6, the top recess 160 of the anti-reflux coupler 125 may include a vent 113, also referred to as an air outlet, and air channels 150a, 150b (collectively "air channels 150") provided in vent groove 114, where the air channels 150 may be notched in a perimeter of the top recess 160 of the anti-reflux coupler 125. As may be appreciated, as the bottom of the reservoir 103 is uniform and without through-holes, the air channels 150 extend past a perimeter of the reservoir 103 and direct air around the side of the reservoir 103.

Figure 8:
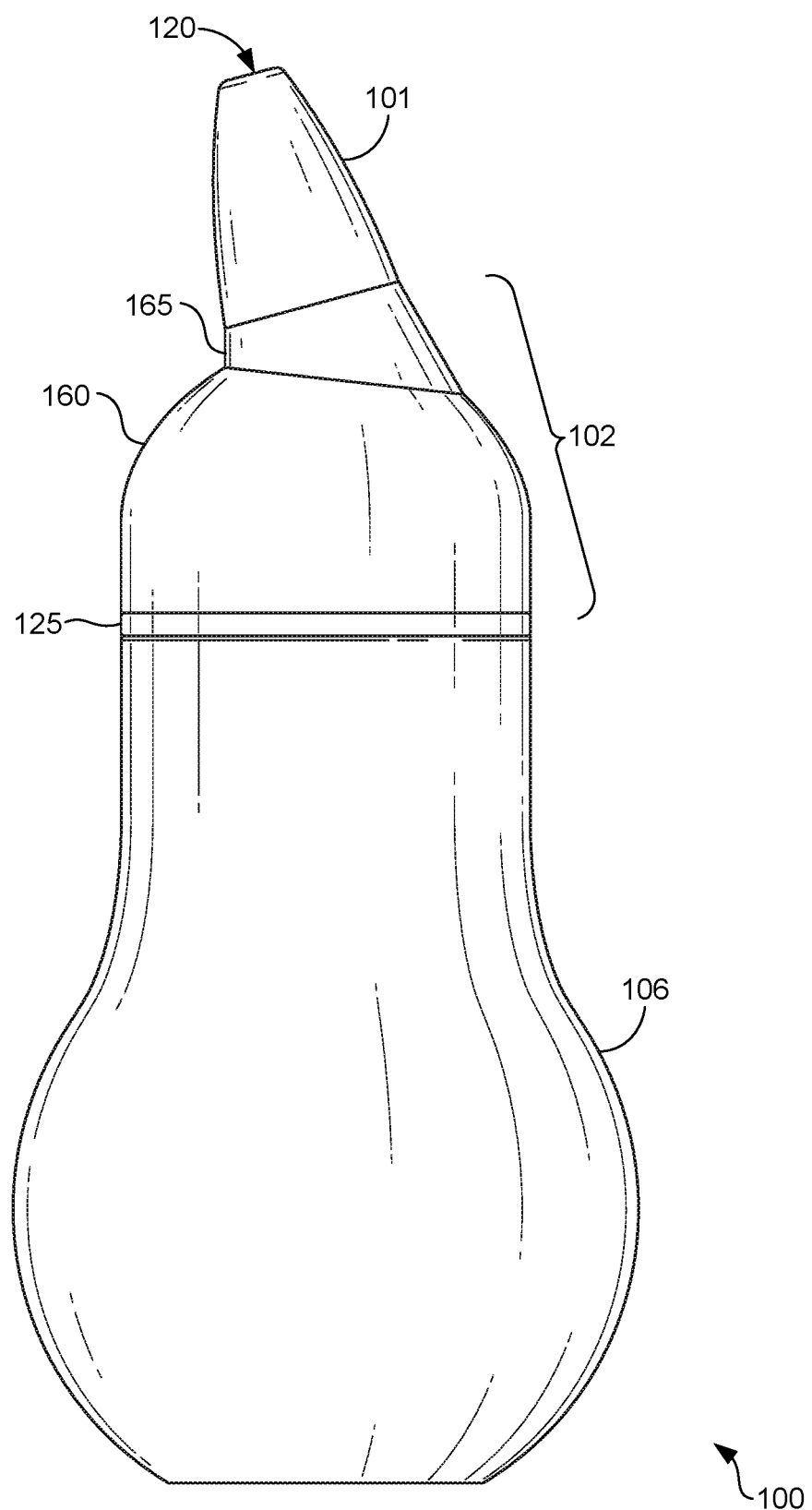
FIG. 8 is a side view of the anti-reflux nasal aspirator according to various embodiments of the present disclosure.
Figure 9:
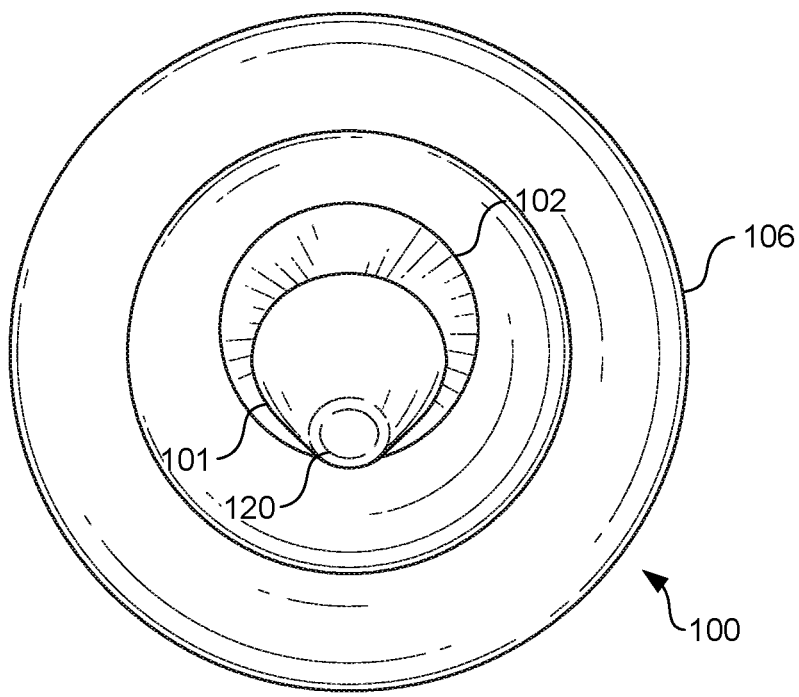
FIG. 9 is a top view of the anti-reflux nasal aspirator according to various embodiments of the present disclosure.
Figure 10:
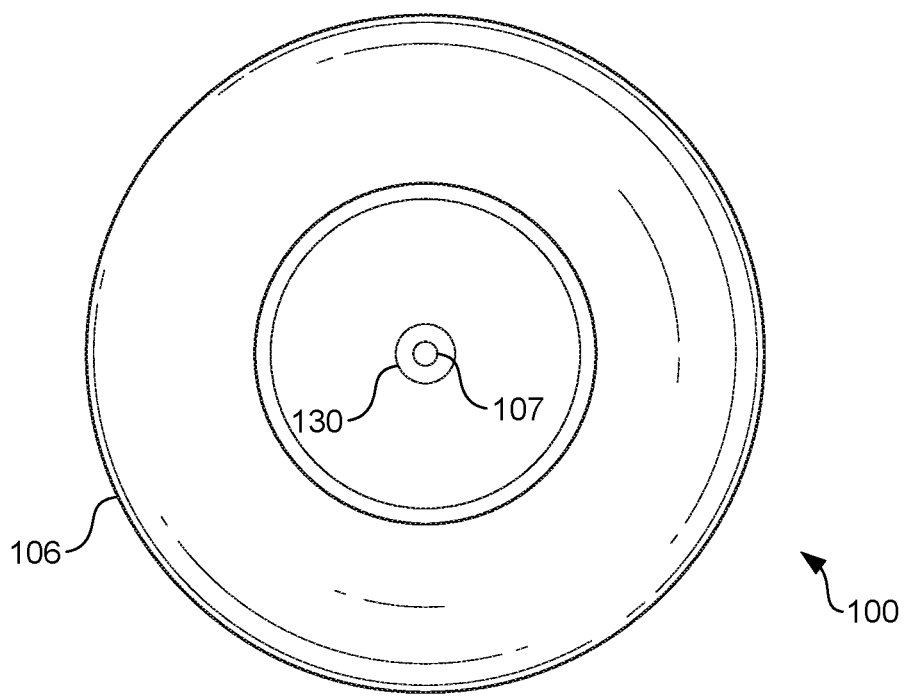
FIG. 10 is a bottom view of the anti-reflux nasal aspirator according to various embodiments of the present disclosure.

Referring now to FIG. 8, in various embodiments, the neck 102 includes a semi-circular base portion 160 having a width substantially similar to a top neck of the bulb 106 and a protruding portion 165 having a width less than the width of the semi-circular base portion 160. The protruding portion 165 can be sized and positioned such that the nozzle 101 is positioned at a predetermined angle such as an angle equal to or less than 90 degrees.

The nozzle 101 may be a first nozzle having a first predetermined size and shape. The anti-reflux nasal aspirator 100 may further include a second nozzle (not shown) having a second predetermined size and shape different from the first predetermined size and shape, the second nozzle being configured to replace the first nozzle via the second connection 140.

The reservoir 103 is used for storing debris, such as snot or other nasal debris, and can be cleaned and used continuously. The reservoir 103 is provided with a reservoir lid 108 to prevent debris from flowing out of a nozzle outlet 120 when the anti-reflux nasal aspirator 100 is tilted or into the interior of the bulb 106. For instance, the check valve 112, which can include a duckbill check valve 112 as shown in FIG. 3, can prevent debris in the nozzle 101 from escaping outward when air or other gas pushes upwards when the bulb 106 is pressed. The one-way air valve 107 can be positioned at the bottom of the bulb 106, which is a one-way air outlet valve through which air in the bulb 106 can be vented when the bulb 106 is squeezed or pressed by the operator.

Accordingly, embodiments of the present disclosure describe an anti-reflux nasal aspirator 100 that includes a bulb 106. An internal thread connector 105 may be provided in the middle of the upper portion of the bulb 106. An external thread connector 104 may be provided outside of the internal thread connector 105. A duckbilled check valve 112, or other type of check valve 112, may be provided at the bottom of the middle portion of the external thread connector 104. The reservoir 103 may be provided at the top of the external thread connector 104. A reservoir lid 108 may be provided at the mouth of the reservoir 103. An external cover, i.e., the neck 102, may be provided outside the reservoir 103.

A nozzle 101 is provided at the upper portion of the external cover, i.e., the neck 102. A first sealing ring 109 may be provided between the neck 102 and the external thread connector 104. Also, a gasket may be provided between the internal thread connector 105 and the external thread connector 104. A one-way air valve 107 may be provided in the middle of the bottom or base of the bulb 106. The embodiments described herein relate to an improved nasal aspirator that it can better contain debris and can effectively prevent reflux. It is convenient to operate and clean, and is suitable for use on many occasions.

The bulb 106 described herein can be continuously pressed and, as such, can bounce back quickly by virtue of a one-way air valve 107 positioned, for instance, at a bottom of the bulb 106. The anti-reflux nasal aspirator described herein provides little or no leakage despite the ability of the nozzle being removeable from the neck 102, the neck being removable from the anti-reflux coupler 125, and the anti-reflux coupler 125 being removable from the bulb 106. An improved nozzle 101 is provided without a flash or welding line, that can be uncomfortable for users. Finally, the anti-reflux nasal aspirator 100 is configured to be easily disassembled, which facilitates cleaning or quick changing of various components. Additional benefits may become apparent after a full viewing of the present disclosure.

The nozzle 101 comprising the nozzle outlet 120 can be fluidly coupled to the neck 102, the reservoir 103, and the anti-reflux coupler 125. The term "fluidly coupled" may refer to the respective components as being physically connected to while permitting debris, including solid or liquid debris or cleansing solution, to pass in a one-directional or two-directional manner (e.g., depending on the presence, or lack thereof, of the check valve 112). The bulb 106 is configured to, in response to a squeezing force applied to the bulb 106, direct air through the neck 102 and the nozzle 101, which creates a sucking force (e.g., suction) at the nozzle outlet 120.

The features, structures, or characteristics described above may be combined in one or more embodiments in any suitable manner, and the features discussed in the various embodiments are interchangeable, if possible. In the following description, numerous specific details are provided in order to fully understand the embodiments of the present disclosure. However, the person skilled in the art will appreciate that the technical solution of the present disclosure may be practiced without one or more of the specific details, or other methods, components, materials, and the like may be employed. In other instances, well-known structures, materials, or operations are not shown or described in detail to avoid obscuring aspects of the present disclosure.

Although the relative terms such as "on," "below," "upper," and "lower" are used in the specification to describe the relative relationship of one component to another component, these terms are used in this specification for convenience only, for example, as a direction in an example shown in the drawings. It should be understood that if the device is turned upside down, the "upper" component described above will become a "lower" component. When a structure is "on" another structure, it is possible that the structure is integrally formed on another structure, or that the structure is "directly" disposed on another structure, or that the structure is "indirectly" disposed on the other structure through other structures.

In this specification, the terms such as "a," "an," "the," and "said" are used to indicate the presence of one or more elements and components. The terms "comprise," "include," "have," "contain," and their variants are used to be open ended, and are meant to include additional elements, components, etc., in addition to the listed elements, components, etc. unless otherwise specified in the appended claims. The terms "first", "second", etc. are used only as labels, rather than a limitation for a number of the objects.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications Therefore, the following is claimed:

1. An anti-reflux nasal aspirator, comprising:
   a nozzle comprising a nozzle outlet;
   a bulb configured to, in response to a squeezing force applied to the bulb, provide suction at the nozzle outlet;
   a neck positioned between the nozzle and the bulb, the neck having a reservoir positioned therein for storing debris pulled from the nozzle outlet;
   an anti-reflux coupler positioned within the bulb through which air passes from the bulb to the nozzle, the anti-reflux coupler comprising a check valve configured to prevent reflux of debris into the bulb, wherein the reservoir is at least partially nested in a top recess of the anti-reflux coupler;
   a first connection for detachably attaching the anti-reflux coupler to the bulb;
   a second connection for detachably attaching the nozzle to the anti-reflux coupler; and
   a one-way air valve positioned in an aperture located at a base of the bulb.

2. The anti-reflux nasal aspirator of claim 1, wherein the neck comprises:
   a semi-circular base portion having a width substantially similar to a top neck of the bulb; and
   a protruding portion having a width less than the width of the semi-circular base portion, wherein the protruding portion positions the nozzle at a predetermined angle, the predetermined angle being equal to or less than 90 degrees.

3. The anti-reflux nasal aspirator of claim 1, wherein:
   the top recess of the anti-reflux coupler comprises an air outlet and air channels notched in a perimeter of the top recess, the air channels directing air around a side of the reservoir.

4. The anti-reflux nasal aspirator of claim 1, further comprising a reservoir lid positioned on a top portion of the reservoir, the reservoir lid comprising a projecting aperture for receiving debris.

5. The anti-reflux nasal aspirator of claim 1, further comprising:
   a first sealing ring configured to prevent leakage occurring at the first connection; and
   a second sealing ring configured to prevent leakage occurring at the second connection.

6. The anti-reflux nasal aspirator of claim 1, wherein the first connection or the second connection is one of: a threaded connection and an interference fit connection.

7. The anti-reflux nasal aspirator of claim 1, wherein the check valve comprises one of: an umbrella valve; a duckbill valve; a slit-cutting valve; and a flapper valve.

8. An anti-reflux nasal aspirator, comprising:
   a nozzle comprising a nozzle outlet;
   a bulb configured to, in response to a squeezing force applied to the bulb, provide suction at the nozzle outlet;
   a neck positioned between the nozzle and the bulb, the neck having a reservoir positioned therein for storing debris pulled from the nozzle outlet; and
   an anti-reflux coupler positioned within the bulb through which air passes from the bulb to the nozzle, the anti-reflux coupler comprising a check valve configured to prevent reflux of debris into the bulb, wherein the reservoir is at least partially nested in a top recess of the anti-reflux coupler.

9. The anti-reflux nasal aspirator of claim 8, further comprising:
   a first connection for detachably attaching the anti-reflux coupler to the bulb; and
   a second connection for detachably attaching the nozzle to the anti-reflux coupler.

10. The anti-reflux nasal aspirator of claim 8, further comprising a one-way air valve positioned in an aperture located at a base of the bulb.

11. The anti-reflux nasal aspirator of claim 8, wherein the neck comprises:
    a semi-circular base portion having a width substantially similar to a top neck of the bulb; and
    a protruding portion having a width less than the width of the semi-circular base portion, wherein the protruding portion positions the nozzle at a predetermined angle, the predetermined angle being equal to or less than 90 degrees.

12. The anti-reflux nasal aspirator of claim 8, wherein:
    the top recess of the anti-reflux coupler comprises an air outlet and air channels notched in a perimeter of the top recess, the air channels directing air around a side of the reservoir.

13. The anti-reflux nasal aspirator of claim 12, further comprising a reservoir lid positioned on a top portion of the reservoir, the reservoir lid comprising a projecting aperture for receiving debris.

14. The anti-reflux nasal aspirator of claim 8, further comprising:
    a first sealing ring configured to prevent leakage occurring at the first connection; and
    a second sealing ring configured to prevent leakage occurring at the second connection.

15. The anti-reflux nasal aspirator of claim 9, wherein the first connection or the second connection is one of: a threaded connection and an interference fit connection.

16. The anti-reflux nasal aspirator of claim 8, wherein the check valve comprises one of: an umbrella valve; a duckbill valve; a slit-cutting valve; and a flapper valve.

17. A method, comprising:
    providing an anti-reflux nasal aspirator, comprising:
      a nozzle comprising a nozzle outlet;
      a bulb configured to, in response to a squeezing force applied to the bulb, provide suction at the nozzle outlet;
      a neck positioned between the nozzle and the bulb, the neck having a reservoir positioned therein for storing debris pulled from the nozzle outlet; and
      an anti-reflux coupler positioned within the bulb through which air passes from the bulb to the nozzle, the anti-reflux coupler comprising a check valve configured to prevent reflux of debris into the bulb, wherein the reservoir is at least partially nested in a top recess of the anti-reflux coupler.

18. The method of claim 17, wherein the top recess of the anti-reflux coupler further comprises an air outlet and air channels notched in a perimeter of the top recess, the air channels directing air around a side of the reservoir.

19. The method of claim 17, wherein the nozzle is a first nozzle and the method further comprises replacing the first nozzle with a second nozzle.

20. The method of claim 19, wherein the second nozzle has a size and shape different from that of the first nozzle.

* * * * *